United States Patent [19]

Keeler et al.

[11] Patent Number: 5,443,831

[45] Date of Patent: Aug. 22, 1995

[54] GENE ENCODING GLYCOPROTEIN B OF INFECTIOUS LARYNGOTRACHEITIS VIRUS

[75] Inventors: Calvin L. Keeler; David J. Poulsen, both of Newark, Del.

[73] Assignee: University of Delaware, Newark, Del.

[21] Appl. No.: 156,866

[22] Filed: Nov. 19, 1993

Related U.S. Application Data

[63] Continuation of Ser. No. 788,123, Oct. 29, 1991.

[51] Int. Cl.$^6$ ............... A61K 39/245; A61K 39/275; C12N 15/38; C07K 14/03

[52] U.S. Cl. .................... 424/199.1; 424/93.2; 424/229.1; 424/232.1; 424/816; 435/69.1; 435/69.3; 435/172.3; 435/252.3; 530/395

[58] Field of Search .............. 424/89, 229.1, 199.1.816.232.1.93.2; 435/172.3, 252.3, 69.1, 69.3; 530/395, 650

[56] References Cited

U.S. PATENT DOCUMENTS

| 4,980,162 | 12/1990 | Honda et al. | 424/202.1 |
| 5,093,258 | 3/1992 | Cohen | 435/235.1 |

FOREIGN PATENT DOCUMENTS

2220941  1/1990  United Kingdom .
8903429  4/1989  WIPO ............... C12P 21/00
WO90/02802  3/1990  WIPO .
WO92/03554  3/1992  WIPO .

OTHER PUBLICATIONS

Whalley et al, J. Gen. Virol 70:383–394, 1989.
Cantin et al, Proc. Natl. Acad. Sci. 84:5908–5912, 1987.
Spoerel, N. A. et al (87) Methods in Enzym. 152: 598–603.
Kongsuwan, K. et al (1991) Virology 184: 404–410.
Griffin, A. M. et al (1991) J. Gen. Virol. 72: 393–398.
Finkelstein, A. et al (1989) Trends in Biotech. 7:273–277.
York, J. J. et al (1990) Arch. Virol. 115:289–297.
Griffin, J. Gen. Vir. 70:3085 (1989).
Griffin & Boursnell, J. Gen. Vir. (1990) (90b).
Nunberg et al., J. Vir. 63:3240 (1989).
York et al., Virology 161:340 (1987).

*Primary Examiner*—Christine M. Nucker
*Assistant Examiner*—Julie Krsek-Staples
*Attorney, Agent, or Firm*—Connolly and Hutz

[57] ABSTRACT

An isolated nucleic acid molecule encoding the gB glycoprotein of Infectious Laryngotracheitis Virus is disclosed. Also disclosed is incorporation of the gB gene into recombinant avipox virus for a vaccine used to immunize fowl.

9 Claims, 2 Drawing Sheets

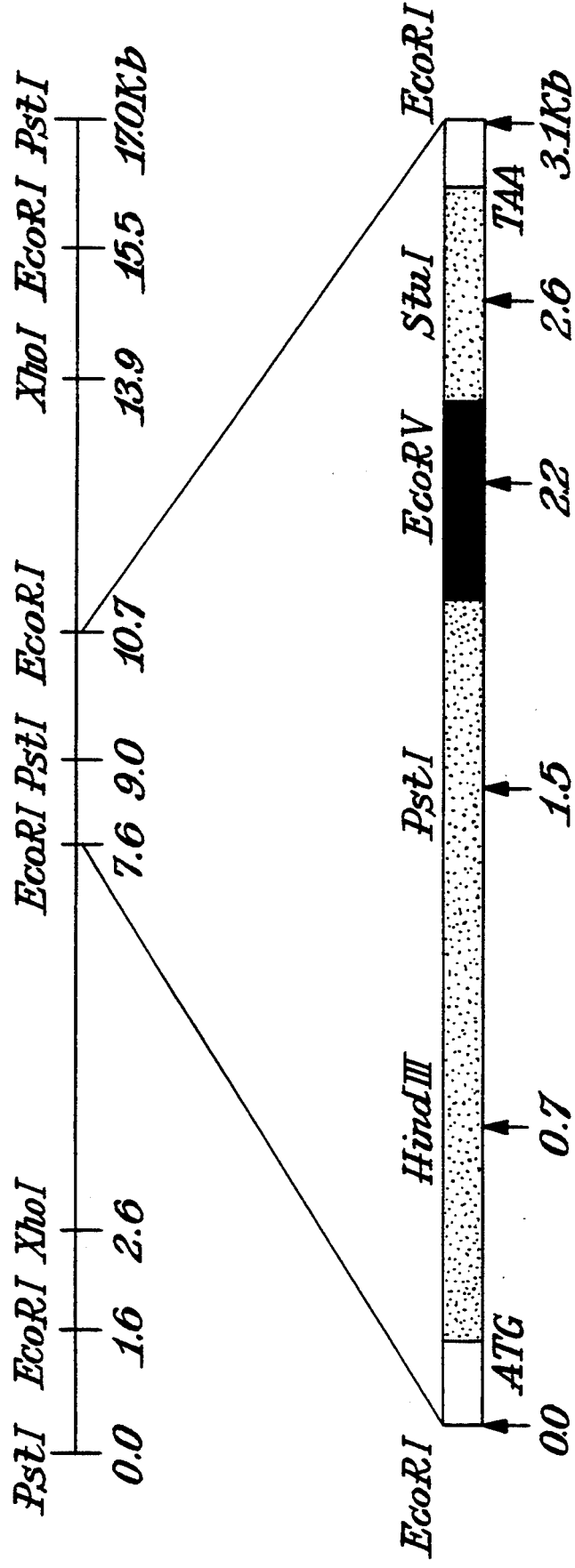

– 5,443,831 –

GENE ENCODING GLYCOPROTEIN B OF INFECTIOUS LARYNGOTRACHEITIS VIRUS

This application is a continuation of application Ser. No. 07/788,123 filed on Oct. 29, 1991.

FIELD OF THE INVENTION

The invention relates to molecular biology, and in particular, to the isolation, sequencing and use of a viral glycoprotein gene. The gene comprises the nucleic acid sequence encoding an envelope glycoprotein of Infectious Laryngotracheitis Virus which is homologous to the gB glycoprotein of Herpes Simplex Virus, Type 1. The invention further relates to use of the viral gene including the preparation and use of certain novel products obtained from the isolated gene.

BACKGROUND AND PRIOR ART

Infectious Laryngotracheitis Virus (ILTV) is the active agent of infectious laryngotracheitis (ILT). ILT is an acute respiratory disease of poultry of global economic significance in terms of mortality and loss of egg production. The clinical symptoms of ILT can vary, and both "mild" and "severe" forms of the disease have been reported.

ILTV is a herpes virus of the alpha herpes virus subfamily. The double-stranded DNA viral genome contains approximately 160 kb pairs of DNA which has not, as yet, been fully sequenced or characterized. See generally, Kotiw et al., Avian Dis. 26:718 (1982); Leib et al., Arch. Virol. 93:287 (1987); Roizman et al., Intervirology 16:201 (1981). Previous molecular studies of the viral genome have focused largely on examining restriction endonuclease digestion patterns prepared from different field isolates of the virus. Andreasen et al., Avian Dis. 34:646 (1990); Guy et al., Avian Dis. 33:316 (1989); Kotiw et al., Avian Dis. 26:718 (1982); Kotiw et al., Vet. Microbiol. 11:319 (1986); Leib et al., Avian Dis. 30:835 (1986). In terms of sequence, the sequence of fragments of certain ILTV genes, identified through random sequencing of genomic ILTV DNA, is reported in Griffin et al., J.Gen. Vir. 70:3085 (1989). Insofar as is known, the only ILTV genes to be fully sequenced are the thymidine kinase (TK) gene, Griffin et al., J.Gen. Vir. 71:841 (1990), and the capsid p40 gene, Griffin, Nucl. Acids Res. 18:3664 (1990).

In herpesviruses, viral glycoproteins are involved in the processes of virus infection, maturation and transmission. Certain viral glycoproteins are not essential for viral growth, and are more likely related to viral tropism. Certain viral glycoproteins of ILTV have been preliminarily characterized based on molecular weight and reactivity with monoclonal antibodies. York et al., Virology 161:340 (1987). Cloning and sequencing of any full-length ILTV glycoprotein gene has not been reported.

There is evidence that herpesvirus glycoproteins are involved in interactions between the virus and the immune system of an infected host animal during the course of infection and in the development of immunity. See, for example, Glorioso et al., J. Immunol. 135:575 (1985); Roizman (ed.), The Herpesviruses, Plenum Publishing Corp: New York (1984). The gB glycoprotein of Herpes Simplex Virus, Type 1 (HSV-1) has been demonstrated to elicit both humoral and cell-mediated immune responses. Blacklaws et al., J. Gen. Virol. 68:1103 (1987); Blacklaws et al., Virology 177:727 (1990); Manservigi et al., J. Virol. 64:431 (1990); Witmer et al., J. Gen. Virol. 71:387 (1990). The sequence of the HSV-1 gB gene is disclosed in Bzik et al., Virology 133:301 (1984). The HSV-1 gB gene and other HSV-1 glycoprotein genes have been expressed using recombinant vaccinia vectors, Blacklaws et al. (1990), supra, in Bk virus episomal vectors, Manservigi et al., supra, and in adenoviral vectors, Witmer et al., supra. Expression of foreign genes in vaccinia vectors is described in U.S. Pat. Nos. 4,722,848; 4,603,112; 4,769,330; 5,017,487; 5,021,347; and 4,920,213.

The most common approach in use to immunize fowl against ILTV is the use of a live virus vaccine, or the use of infected cultured cells, as disclosed, for example in U.S. Pat. No. 4,980,162 to Honda et al. Live vaccines are not always effective, however, and can be pathogenic even if prepared from low-virulence field isolates.

In the art, viral proteins including viral envelope glycoproteins have been used to prepare subunit vaccines. Subunit vaccines are considered to be a safer alternative in that such vaccines contain no live virus and no viral genetic material. Depending on how it is produced, the viral subunit may or may not be glycosylated. Subunit vaccines based on the HSV gB glycoprotein are disclosed in U.S. Pat. Nos. 4,724,146; 4,661,349; and 4,642,333.

Homologs of the HSV-1 gB gene have been found in a number of different herpesviruses, including pseudorabies virus (PRV), Marek's disease virus (MDV), Varicella zoster virus (VZV), bovine herpes virus type 1 (BHV-1), equine herpesvirus 4 (EHV-4), human cytomegalovirus (HCMV), and Epstein Barr Virus (EBV).

SUMMARY OF THE INVENTION

The invention relates to an isolated nucleic acid sequence comprising the gene encoding the ILTV envelope glycoprotein which is homologous to the gene encoding the gB glycoprotein of HSV-1. The gene is therefore referred to herein as the "ILTV gB glycoprotein gene" or the "ILTV gB gene". The nucleotide sequence of the ILTV gB glycoprotein gene, and the imputed amino acid sequence of the encoded protein, is shown in the appended SEQ ID NO: 1. Isolation of the gene from ILTV genomic DNA using the polymerase chain reaction (PCR) is described. Other aspects of the invention include use of the isolated nucleic acid sequence for production of recombinant protein, production of recombinant vectors, and uses of the recombinant vectors or proteins as vaccines.

BRIEF DESCRIPTION OF THE DRAWINGS

FIG. 2 shows restriction maps of the genomic region containing the ILTV gB gene. FIG. 2(A) discloses a partial restriction map of two contiguous PstI fragments. As described herein, the ILTV gB gene is contained within an EcoRI fragment which spans the two PstI fragments. FIG. 2(B) shows an expanded map of the 3.1 kb EcoRI fragment. Relevant restriction sites identify the five fragments which were cloned and sequenced. The stippled box represents the gB gene, and the shaded box represents the location of the amplified PCR product.

DETAILED DESCRIPTION OF THE INVENTION

Figure 1:
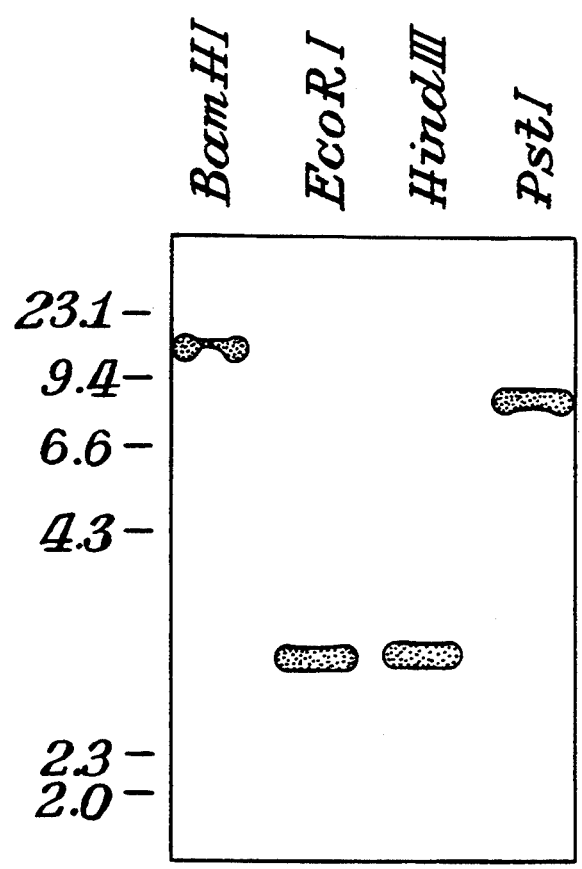
FIG. 1 illustrates genomic localization of the ILTV gB gene. Viral DNA was digested with the indicated restriction enzymes and the resulting fragments were electrophoresed on a 0.8% agarose gel and blotted onto a nitrocellulose membrane. The membrane was hybridized with a $^{32}$P-labeled probe corresponding to the 488 bp PCR fragment described herein. The positions of DNA markers (in kbp) are indicated in the left margin.

For purposes of this disclosure, the ILTV gB gene refers primarily to the molecule having the nucleotide sequence shown in SEQ ID NO: 1, and more particularly, to the portions of that sequence which actually encode polypeptide. The gene sequence as herein contemplated embraces certain variations of the gene sequence. For example, naturally-occurring allelic forms of the gene would be encountered in different ILTV strains. The different allelic forms of the ILTV gB glycoprotein gene present in the various strains and isolates of ILTV, including both field and laboratory strains as well as attenuated mutants, would be expected to be substantially homologous to the sequence of SEQ ID NO: 1 and to encode a functionally identical or similar protein product. Other than the natural alleles, other variations, mutants and derivatives of the sequence encompassed by the invention should meet at least one of the following parameters. A variant sequence may include base substitutions which are silent in the encoded polypeptide, or which result in a conservative amino acid substitution in the encoded polypeptide. Different substitutions, deletions, and inversions of the base sequence are contemplated provided that the sequence is substantially full-length at least from the portion encoding from the N-terminus of the protein to the membrane-spanning region, which is the portion of the polypeptide most exposed to immune surveillance by infected cells and thus of most antigenic significance. Any variant of the sequence shown in SEQ ID NO: 1 should be sufficiently homologous as to be specifically hybridizable, under moderate hybridization conditions, with ILTV gB DNA or RNA. For example, a sequence containing certain bases which differ from wild-type (or from the sequence shown in SEQ ID NO: 1) may still be sufficiently homologous to be useful as a gB-specific probe in Southern or Northern blots, or in the case of the strand complementary to the gB transcript, to bind specifically to gB RNA and find potential utility in antisense control of gB gene expression. Any fragment of the gene of sufficient length and homology to the sequence will find utility as a probe, provided that sufficient length and sequence homology are retained to permit specific hybridization to ILTV gB DNA or RNA. For purposes of the disclosure, the ILTV gB protein shall refer to the amino acid sequence shown in SEQ ID NO: 1, in either glycosylated or unglycosylated form, and also to mutants, derivatives or fragments of the primary sequence. Mutants include substitutions, additions or deletions of one of more amino acid residues. A derivative of the protein includes, for example, a fusion of the protein sequence to a heterologous protein sequence such as $\beta$-galactosidase. Fragments of the polypeptide sequence refers to portions of the complete amino acid sequence, which are either synthesized directly from corresponding fragments of the gene sequence, or are obtained by enzymatic cleavage of the full-length polypeptide, or are prepared synthetically, for example by solid phase peptide synthesis. Mutants and fragments of the ILTV gB protein which are sufficiently immunogenic to elicit an anti-ILTV response in vivo or in vitro are most preferred. As the topology, folding and conformational structure of viral glycoproteins becomes more fully understood, it will be possible to predict important immunogenic epitopes directly from the primary protein structure. Future developments may also reveal in more detail how viral antigens are processed and presented by infected cells, allowing for prediction of the important viral epitopes which most effectively elicit a response by immune effector cells.

An additional class of mutant sequences contemplates the modification of the nucleotide sequence to delete the transcriptional terminator sequences which would be active in a recombinant viral vector, such as fowl pox, as described herein. In some cases this may be done without altering the amino acid of the encoded product.

As described in the examples which follow, the gene sequence shown in SEQ ID NO: 1 was isolated from ILTV genomic DNA using the polymerase chain reaction (PCR). PCR technology is well-known in the art and is not described in detail herein. See, for example, U.S. Pat. Nos. 4,683,202; 4,683,195; 4,889,818. See also, Innis et al. (Eds.), PCR Protocols: A Guide to Methods and Applications, Academic Press: New York (1989). The isolation strategy used by Applicants involved use of degenerate primers, which were designed based on conserved amino acid sequences in herpes viruses related to ILTV. However, not all primers so designed were successful in yielding DNA fragments of the expected size. One pair of PCR primers which were successful in permitting isolation of ILTV gB DNA are disclosed in Example 1 which follows. It will be understood, however, that additional means of isolating ILTV gB DNA are enabled to those skilled in the art by the sequence data disclosed herein. For example, the sequence data herein enables synthesis or use of probes of sufficient specificity to isolate the gB glycoprotein gene or fragments directly from digested ILTV genomic DNA or a DNA library. It is noted that heterologous probes comprising the gB gene of other herpesviruses, including HSV-1, MDV, VZV, BHV-1, EHV-4, HCMV, and EBV, are not sufficiently homologous to ILTV gB to allow recovery of the ILTV gene using the heterologous gB gene to probe ILTV genomic DNA. Moreover, the sequence data disclosed herein enables one skilled in the art to design alternate, highly-specific PCR primers to achieve recovery of the gB gene from ILTV genomic DNA.

Referring to the sequence shown in SEQ ID NO: 1, analysis of the isolated sequence identified a single 2619 bp open reading frame with an ATG codon 185 bp downstream from the beginning of the sequenced region. The predicted translation product of the ILTV open reading frame would correspond to an unmodified protein of 873 amino acids, which is approximately the size of the gB homologues of MDV and VZV, which are 865 and 868 amino acids respectively. See, Ross et al., J. Gen. Virol. 70:1789 (1989); Keller et al., Virology 152:181 (1986). Two potential in-frame initiation codons can be predicted for the open reading frame. The second ATG is currently considered the most likely, since its local environment favors the modified scanning model of translation and provides for the characteristic features of a signal sequence. See, Kozak, Microbiol. Rev. 47:1 (1983); von Heijne, Nucl. Acids Res. 14:4683 (1986). The termination codon for an open reading frame showing homology to the HSV-1 ICP18.5 gene occurs one nucleotide before the predicted ILTV gB initiation codon. The ICP18.5 protein of HSV-1 has been reported to be involved in viral glycoprotein transport and the gene terminates 10 nucleotides before the initiation codon of the gB gene. Pellet et al., J. Virol. 60:1134 (1986). ICP18.5 homologues have been shown to overlap with the PRV gII, EHV-4 gB and BHV-1 gB protein coding sequences by 132, 135 and 141 nucleotides respectively. Misra et al., Virology 166:542 (1988). Riggio et al., J. Virol. 63:1123 (1989); Robbins et al., J. Virol. 61:2691 (1987). A potential TATA box (TA-TATTT) was found which aligns well with the TATA boxes of MDV, EHV-4, PRV and BHV-1. A potential polyadenylation signal (AATAAA) is located 23 nucleotides downstream from the end of the ILTV open reading frame.

The ILTV gB protein predicted from the DNA sequence shares features with the envelope glycoproteins of other herpesviruses, including a putative signal sequence at the amino terminus and a membrane-spanning hydrophobic region near the carboxy terminus. Based on the criteria of Perlman and Halvorson, J. Mol. Biol. 167:391 (1983) and von Heijne, supra, the potential ILTV gB signal sequence domain is similar to that predicted for MDV, another avian herpesvirus. An 11 amino acid hydrophobic core is found from amino acids 6 to 16. The Val-Val pair usually conserved in eucaryotic signal sequences at core positions 7 and 8 is replaced by Val-Ala in ILTV gB. However, this is consistent with the observed signal domains of the gB homologues in PRV, MDV and EHV-4. Immediately following the hydrophobic core, Pro and Thr are observed at positions 17 and 19 respectively. This results in a disruption of the predicted $\beta$-extended strand structure of the core and agrees with conserved features among eucaryotic signal sequences. The signal cleavage site is predicted to occur four residues after Pro-17, following the second Ser in the sequence Pro-Ser-Thr-Leu-Ser. The mature ILTV protein is then predicted to begin with Gln-22.

Eight potential N-linked glycolylation sites (Asn-X-Ser/Thr) are present in the external surface domain of the ILTV protein. The positions of four of these are conserved with respect to the HSV-1 gB protein. Furthermore, all 10 cysteine residues outside of the signal sequence are conserved with respect to all known gB homologues. In addition, the sequence Arg-Glu-Arg-Arg at position 425 to 428 of the ILTV protein is identical to the demonstrated or proposed proteolytic cleavage sites (Arg-X-Arg-Arg) for a number of gB homologues. See Keller et al., supra; Misra et al., supra; Robbins et al., supra; Ross et al., supra; Spaete et al., Virology 67:207 (1988); Spaete et al., J. Virol. 64:2922 (1990); Whealy et al., J. Virol. 64:1946 (1990).

Hydropathic and secondary structure analysis of the ILTV open reading frame predict a hydrophobic 68 amino acid stretch from position 696 to 764. Hydropathic profiles indicate that this region may traverse the membrane three times, a common motif of previously identified gB homologues. The remaining 109 amino acids of the predicted protein, including a stretch of 88 hydrophilic amino acids, could function as the cytoplasmic anchor. In agreement with the proposed cytoplasmic domains of HSV-1, PRV, and EHV-4, the predicted secondary structure of this ILTV segment has high alpha-helix-forming potential.

The predicted translation product of the ILTV open reading frame was compared to the gB glycoproteins reported for other herpesviruses. The ILTV protein was more closely related to HSV-1 (38%), PRV (39%) and MDV (39%) than to the betaherpesvirus HCMV (29%) and the gammaherpesvirus EBV (28%).

The presence of ILTV immunogenic epitopes or antigenic determinants on the ILTV gB glycoprotein makes the recombinant gB protein, or expression vectors comprising the gB gene in a manner which can be expressed in vivo, potentially useful in immunization of fowl, particularly chickens, in which ILT is a serious problem. The isolated gene sequence, together with techniques available in the art, fully enables these uses of the ILTV gB gene. Use of the sequence described herein includes expression of the ILTV gB gene or fragments of the gene encoding one or more of the viral antigenic determinants. The expressed gene products and recombinant vectors are useful in prophylactic and therapeutic immunization of fowl. Particularly preferred embodiments comprise: 1) incorporation of the isolated gB gene or any antigen-encoding portion or fragment of the gene into recombinant viral vectors for expression of the gB gene in vivo in a live vaccine; and 2) expression of the recombinant polypeptide or fragments and subsequent formulation of the recombinant gene products into vaccine preparations for administration to fowl using conventional immunization protocols.

The isolated gene of the invention may be propagated and amplified in commercially available cloning vectors. For example, the gene may be cloned into a replicable plasmid and amplified by transforming bacteria with the plasmid.

A first embodiment of using the gB gene involves expressing the gB gene from a recombinant viral or bacterial vector as a live vaccine. The parent virus or bacteria is preferably one which normally infects poultry. Techniques for preparing recombinant viral vectors, and for use of the recombinant vectors as vaccines, are known in the art. Briefly, "non-essential" sequences in the parent virus (or bacteria) are replaced by homologous recombination with the heterologous gene under control of an active promoter. "Non-essential sequences" refer to sequences not essential to viability or growth of the parent virus under at least some growth conditions, such as growth in tissue culture. Non-essential sequences may be replaced or interrupted without ablating the ability to form infectious recombinant virions within the recombination host cell, which virions, when recovered, remain fully infectious. Such sequences have been identified and mapped in a number of important viruses. To form the recombinant vector, a recombination construct is provided, in the form of linear or plasmid DNA comprising the heterologous gene with the associated control sequences (e.g. promoter), flanked by sequences homologous to the nonessential sequences being targeted in the parent virus, and optionally selection markers. Within the recombination host cell, homologous recombination events between the recombination construct and the parent virus insert the heterologous gene into the parent virus to produce the recombinant virus.

Preferred viral vectors are fowlpox, vaccinia, adenovirus, Marek's Disease Virus, and Herpes Virus of Turkeys (HTV). Reference is made to the following disclosures concerning exemplary recombinant vectors, their preparation and their use as vaccines. Recombinant vaccinia virus is described in U.S. Pat. Nos. 4,722,848; 4,603,112; 4,769,330; 5,017,487; 5,021,347; and 4,920,213. As therein described, a heterologous gene is inserted into a nonessential region of the vaccinia genome, such that the recombinant virus retains full infectivity and the heterologous gene is efficiently expressed in vivo to elicit an immune response.

The gB gene may also be expressed from other recombinant pox viruses, such as fowlpox virus. Fowlpox virus non-essential regions are disclosed, for example, in UK Patent Application 2,220,941 A, published Jan. 24, 1990. As disclosed therein, the foreign gene is inserted transcribably downstream of a promoter, preferably a fowlpox virus promoter such as the "4b" or "13.2K" promoters, to which fowlpox virus RNA polymerase will bind and transcribe the foreign gene. Further disclosure of constructing recombinant fowlpox, and the use thereof to confer protective immunity to viral pathogens upon chickens, is found in Boursnell et al., J. Gen. Vir. 71:621 (1990); Boyle and Coupar, Virus Research 10:343 (1988); and Taylor et al., Vaccine 6:504 (1988). Recombinant fowlpox is a particularly desirable form of vector in that its administration can confer protective immunity against both ILTV and FPV.

As noted, the nucleic acid sequence of the gB gene may be modified, e.g. by site-directed mutagenesis, to optimize the gene sequence for a particular vector or expression system, for example to enhance expression or facilitate secretion. Mutagenesis may be used to delete or change transcriptional terminator sequences which are active in a viral vector.

The invention relates further to expression of the gB gene sequence or gene fragments encoding immunogenic protein fragments, using a suitable expression system, and to use of the recovered recombinant protein or peptide for immunization or immunoassay.

Preferred host cells for expression include bacteria, particularly *E. coli* and *B. subtilis*, yeast, in particular *S. cerevisiae*, mammalian cells such as CHO, HeLa, or fibroblasts, and insect cells. Expression protocols are known in the art and are not described in detail. Reference is made to the following references illustrating the preparation of expression constructs, expression of the constructs in prokaryotic or eukaryotic hosts, and recovery of the protein product from the host cells or the associated culture medium: Berger and Kimmel, Methods in Enzymology, Vol. 152, Academic Press (1987); Ausubel et al. (eds.), Current Protocols in Molecular Biology, Greene Publishing and Wiley Interscience:- New York (1990); Sambrook et al., Molecular Cloning, A Laboratory Manual, Cold Spring Harbor Laboratory: Cold Spring Harbor, N.Y. (1989). The skilled artisan will be enabled by the sequence data herein to express recombinant ILTV gB protein and recover the expressed protein. See also, U.S. Pat. Nos. 4,642,333; 4,761,371; 4,940,661; 4,925,793; and 4,853,330.

When expressed in bacteria, the recombinant protein will lack the polysaccharide component of native protein (glycosylation). To obtain a recombinant peptide which is post-translationally modified, it may be preferable to express the ILTV gB gene in a eukaryotic host cell, such as yeast or insect cells. Expression of heterologous genes in these eukaryotic host cells is known in the art. Yeast expression is disclosed, for example, in U.S. Pat. No. 4,977,092; and in Guthrie et al. (Eds.), Guide to Yeast Genetics and Molecular Biology, Academic Press (1990). Expression in insect cells using a baculoviral vector is disclosed in U.S. Pat. Nos. 4,879,236; 4,745,051; and 5,023,328. See also, Miller, Ann. Rev. Microbiol. 42:177 (1988).

A preferred use of the gB gene is to express recombinant gB polypeptide, either glycosylated or unglycosylated, for use of the recombinant protein in a subunit vaccine. Although the entire gene may be expressed, it is also possible to express only portions of the gB protein, particularly immunogenic portions, i.e. those portions of the gB protein capable of eliciting an anti-ILTV humoral or cellular response in an inoculated host. One expedient manner of making this determination is to assess whether the recombinant product is immunologically cross-reactive with natural gB protein. For example, cells expressing the recombinant product can be screened with labeled anti-gB antibodies (serum) or monoclonal antibodies, or the cell preparations containing recombinant peptide could be analyzed by immunoassay or immune precipitation.

One particular antigenic fragment of interest is produced by deleting the sequence encoding the cytoplasmic C-terminal domain, the signal sequence, and the membrane-spanning domain. The remaining portions of the sequence encode the portions of the polypeptide most likely to be antigenically active. Based on the nucleotide sequence of the gB gene, and the imputed amino acid sequence of the gB gene product, short peptides of about 10–25 amino acid residues may be expressed (or synthesized synthetically) and screened for immunogenicity.

The recombinant gB protein, or immunogenic peptide fragments coupled to an appropriate carrier, can be used to raise antisera or monoclonal antibodies to the gB protein or certain of its antigenic determinants using known methods. The gB protein and anti-gB antibodies are useful in solid or liquid phase immunoassay. Assays using the recombinant gB protein as reactant can be used, for example, to assay the titer of anti-gB antibody in serum. Anti-gB serum or monoclonal antibodies are useful for detecting or assaying gB expression in an infected cell or host animal. By way of example, anti-gB antibodies or antibody fragments can be labeled with a detectable label, such as a fluorescent marker, to visualize gB glycoprotein expression on the surface of infected cells.

To incorporate the protein or peptide fragment into a vaccine for immunization of fowl, the protein or fragment is incorporated, alone or with other immunogenic proteins, into carrier and/or adjuvant preparations for administration to fowl as a subunit vaccine. Methods of administration include injection (wing web or subcutaneous) or aerosol. Other factors which may influence choice of administration format include the age of the birds, and whether the vaccine is administered together with other vaccines.

Aspects of the invention are shown by the following specific examples, which are provided as illustration and not as limitation on the scope of the invention.

EXAMPLE I

Isolation and Cloning of ILTV gB Using PCR

A comparison of the known amino acid sequences of several alphaherpesvirus gB proteins revealed common conserved regions. Degenerate oligonucleotide primers corresponding to several regions were synthesized. All primers included 9 nucleotide extensions containing restriction endonuclease cleavage sites at their 5' ends. Pairs of degenerate primers were used to initiate PCR on genomic DNA prepared from ILTV virulent field isolate 632. Virus was propagated on monolayers of primary chicken embryonic liver cells prepared by the warm trypsin disaggregation technique of Freshney, In *Culture of Animal Cells, A Manual of Basic Techniques,*

Allan R. Liss: New York, pp. 99–118 (1983). Infected cells were harvested and viral DNA was prepared from Triton X-100-proteinase K-treated cells as described by Pignatti et al., Virology 93:260 (1979).

Polymerase chain reactions (PCRs) were carried out using the thermostable DNA polymerase of *Thermus aquaticus* (Perkin-Elmer Cetus Instruments, Norwalk, Conn.) with primer concentrations at 100 or 200 pM per 50 µl reaction. PCR products were analyzed on 1.2% low melting temperature agarose gels. A pair of the degenerate oligonucleotide primers corresponding to amino acids 613–617 and 772–776 of the published sequence of the gB protein of HSV-1 (as the sequence is reported in Bzik et al., Virology 133:301 (1984)), yielded a 488 bp amplified fragment of the expected size. The PCR product was purified, digested with restriction endonucleases and cloned into a BlueScript plasmid (Stratagene, La Jolla, Calif.) using standard techniques. A double-stranded plasmid template of the PCR-derived clone was sequenced using Sequenase II T7 DNA polymerase (U.S. Biochemicals Corp., Cleveland, Ohio) by the dideoxy chain termination method. Analysis of sequence data showed that the 488 bp PCR fragment shared 52% DNA and 48% amino acid homology to a portion of the HSV-1 gB protein (per Bsik et al., supra) spanning the junction of the external and transmembrane domains (amino acids 797 to 958). Using this portion of the ILTV glycoprotein B gene, the entire gene was localized and cloned. Viral genomic DNA was digested with various restriction enzymes, transferred onto nitrocellulose and hybridized with a $^{32}$P-labeled species of the 488 bp PCR fragment. The radiolabeled probe hybridized to 14.9 kb BamHI, 3.1 kb EcoRI, 3.2 kb HindIII and 8.6 kb PstI fragments, as shown in FIG. 1. Initially, the 8.6 kb PstI and 3.2 kb HindIII fragments were cloned into the BlueScript plasmid vector pKSII-. Restriction mapping of the PstI clone, pDP01, and localization of the PCR amplified fragment within this clone, shown in FIG. 2, indicated that the entire gene was not contained within this one PstI fragment. Consequently, an additional hybridization with the cloned 3.2 kb HindIII fragment, pDP02, identified an adjacent 9.0 kb PstI fragment which was also cloned into pKSII-. Based on the location of the PCR product and the known lengths of other herpesvirus glycoprotein B genes previously characterized, the glycoprotein gB gene of ILTV was predicted to be contained within a 3.1 kb EcoRI fragment spanning the two cloned PstI fragments. See FIG. 2(B). Five restriction fragments from this region, none larger than 800 bp in length, were subcloned in order to facilitate sequencing the gene. Sequencing produced the sequence shown in SEQ ID NO: 1.

EXAMPLE 2

Protection of Chickens from ILTV Challenge using a Recombinant Fowlpox Vector Expressing ILTV gB Experiments were carried out to demonstrate that chickens could be clinically protected from virulent ILTV challenge by the administration of a recombinant fowlpox virus expressing the gB gene of the invention under control of a fowlpox promoter.

To generate the recombinant fowlpox, a 3.1 kb ILTV DNA fragment containing the gB gene was cloned into a vector plasmid containing a functional fowlpox promoter and flanking fowlpox sequences. The gB gene was inserted by homologous recombination using standard techniques into a nonessential region of a commercially available fowlpox vector (CEVA Laboratories) to produce recombinant fowlpox ILTgBH-1.

Eighty 4-week old specific pathogen free (SPF) single comb white leghorns were split into four groups of twenty birds. A first control group received no vaccination. A second group was vaccinated with nonrecombinant fowlpox vector vaccine (CEVA Laboratories) alone. A third group was vaccinated with ILTV strain 632 via eyedrop. The fourth group of twenty received recombinant fowlpox ILTgBH-1 via scarring of the wing web. Birds were then challenged post-vaccination for resistance to challenge by both FPV and ILTV, as follows.

Two weeks post-vaccination ten birds from each group were challenged with the nonrecombinant fowlpox virus vector in the opposite wing web. Resistance to challenge was assessed based on presence or absence of swelling at the challenge site.

Four weeks after the initial vaccinations, the remaining ten birds in each group were challenged by the intrasinous route with $10^4$ EID$_{50}$ of a pathogenic strain of ILTV, strain 632. Birds were observed for clinical signs (sinusitis, watery eyes, gasping, lethargy) for three consecutive days beginning three days post-challenge. Birds scoring negative for clinical signs for two of the three days were considered resistant to the challenge virus.

Results are presented in the following table:

|  | Protection from FPV Challenge | Protection from ILTV Challenge |
| --- | --- | --- |
| Group 1 Unvaccinated Controls | 0% (0/10) | 0% (0/10) |
| Group 2 FPV Vector Vaccine Controls | 100% (10/10) | 12.5% (1/8) |
| Group 3 ILTV Vaccinated Controls | 0% (0/10) | 70% (7/10) |
| Group 4 Recombinant ILTgBH-1 Vaccinated | 100% (10/10) | 80% (8/10) |

The above results reflect that the chickens vaccinated with recombinant fowlpox of the invention expressed the gB protein in vivo and that protective immunity against ILTV was conferred. Not only were the birds protected against FPV challenge, but were also protected against ILTV challenge at least as well as control birds vaccinated with whole ILTV virus.

Each patent and publication cited in the foregoing disclosure is hereby incorporated by reference.

Having thus described the invention, the scope of the invention is set forth in the appended claims:

SEQUENCE LISTING ( 1 ) GENERAL INFORMATION:

( i i i ) NUMBER OF SEQUENCES: 1

( 2 ) INFORMATION FOR SEQ ID NO:1:
    ( i ) SEQUENCE CHARACTERISTICS:
        ( A ) LENGTH: 3065 base pairs
        ( B ) TYPE: Nucleic Acid
        ( C ) STRANDEDNESS: double stranded
        ( D ) TOPOLOGY: linear
        ( i i ) MOLECULE TYPE: Genomic DNA ( i i i ) HYPOTHETICAL: No
    ( i v ) ANTI-SENSE: No
    ( v i ) ORIGINAL SOURCE:
        ( A ) ORGANISM: Gallid Herpesvirus 1
        ( C ) INDIVIDUAL ISOLATE: 632
        ( x i ) SEQUENCE DESCRIPTION: SEQ ID NO:1:

```
GAATTCGACC TCGACGGCCC GATTTTGGAA AACGGGCTAT ATTTAACATT TGAAGAGGAA        60
CATCCATTAG TTGCAGTGTG GGGCGTCGAT GACCGCGGGA AACTGGGTCC AGCGTCTACT       120
ATCATAGTAG AGAAAGATTT ATACGCGGTC CTGTATGCAA TCCTACATCG CCGTGAACAT       180
TGAC ATG GCT AGC TTG AAA ATG CTG ATC TGC GTG TGC GTG GCA ATC CT        229
     Met Ala Ser Leu Lys Met Leu Ile Cys Val Cys Val Ala Ile L
     1               5                  10
ATC CCA TCT ACC CTA TCT CAA GAT TCA CAC GGA ATT GCT GGA ATA ATA        277
Ile Pro Ser Thr Leu Ser Gln Asp Ser His Gly Ile Ala Gly Ile Ile
20                  25                  30
GAC CCT CGT GAT ACA GCC AGC ATG GAT GTT GGA AAA ATC TCT TTC TCC        325
Asp Pro Arg Asp Thr Ala Ser Met Asp Val Gly Lys Ile Ser Phe Ser
35                  40
GAA GCC ATT GGG TCG GGG GCA CCG AAA GACCC CAG ATT AGA AAC AGA          373
Glu Ala Ile Gly Ser Gly Ala Pro Lys Glu Pro Gln Ile Arg Asn Arg
50                  55                  60
ATT TTT GCG TGC TCA TCT CCA ACT GGC C AGT GTT GCG AGG CTT GCC          421
Ile Phe Ala Cys Ser Ser Pro Thr Gly Ala Ser Val Ala Arg Leu Ala
65                  70                  75
CAG CCA CGA CAT TGT CAC CGA CAT GCGAT TCG ACT AAC ATG ACT GAA          469
Gln Pro Arg His Cys His Arg His a Asp Ser Thr Asn Met Thr Glu
80                  85                  90                  95
GGA ATT GCC GTA GTC TTC AACAA AAC ATT GCC CCG TAC GTC TTT AAT          517
Gly Ile Ala Val Val Phe Lys Asn Ile Ala Pro Tyr Val Phe Asn
100                 105                 110
GTG ACT CTA TAC TAT AAA T ATA ACC ACA GTT ACT ACG TGG GCA TTA          565
Val Thr Leu Tyr Tyr Lys His Ile Thr Thr Val Thr Thr Trp Ala Leu
115                 120                 125
TTC TCA AGA CCC CAA ATACA AAT GAG TAC GTG ACC AGG GTT CCA ATA          613
Phe Ser Arg Pro Gln Ile Thr Asn Glu Tyr Val Thr Arg Val Pro Ile
                130                 135                 140
GAC TAT CAT GAA ATT GTC AGG ATT GAT CGA TCG GGA GAA TGC TCA TC         661
Asp Tyr His Glu Ile Val Arg Ile Asp Arg Ser Gly Glu Cys Ser Ser
145                 150                 155
AAA GCA ACG TAT CAT AAA AAT TTC ATG TTT TTT GAA GCT TAC GAC AAT        709
Lys Ala Thr Tyr His Lys Asn Phe Met Phe Phe Glu Ala Tyr Asp Asn
160                 165                 170                 175
GAT GAA CGA GAA AAA AAA TTG CCC CTG GTT CCA TCA CTG TTA AGA TCA        757
Asp Glu Arg Glu Lys Lys Leu Pro Leu Val Pro Ser Leu Leu Arg Ser
180                 185                 190
ACT GTC TCC AAG GCG TTT CAT ACA ACT AAC TTT ACT AAG CGA CAT CAA        805
Thr Val Ser Lys Ala Phe His Thr Thr Asn Phe Thr Lys Arg His Gln
195                 200                 205
ACC CTG GGA TAC CGA ACG TCT ACA TCG GTC GAC TGT GTT GTG GAA TAT        853
Thr Leu Gly Tyr Arg Thr Ser Thr Ser Val Asp Cys Val Val Glu Tyr
210                 215                 220
CTA CAG GCT AGA TCT GTA TAC CCG TAT GAT TAC TTT GGA ATG GCG ACC        901
Leu Gln Ala Arg Ser Val Tyr Pro Tyr Asp Tyr Phe Gly Met Ala Thr
225                 230                 235
GGT GAT ACA GTA GAA ATT TCT CCT TTT TAT ACC AAA AAC ACG ACC GGA        949
Gly Asp Thr Val Glu Ile Ser Pro Phe Tyr Thr Lys Asn Thr Thr Gly
240                 245                 250                 255
    AGT GTC TAC AGA GAC TAT AGA TTT CTC GAA ATC GCA              997
    Pro Arg Arg His Ser Val Tyr Arg Asp Tyr Arg Phe Leu Glu Ile Ala
260                 265                 270
AAT TAT CAA GTC AGG GAT TTG GAA ACC GGA CAA ATA AGA CCC CCT AAA       104
Asn Tyr Gln Val Arg Asp Leu Glu Thr Gly Gln Ile Arg Pro Pro Lys
275                 280                 285
AAA AGA AAC TTT CTA ACA GAT GAA CAA TTC ACT ATA GGC TGG GAT GCA       1093
Lys Arg Asn Phe Leu Thr Asp Glu Gln Phe Thr Ile Gly Trp Asp Ala
290                 295                 300
ATG GAA GAA AAG GAA TCT GTA TGT ACT CTC AGT AAA TGG ATT GAA GTC       1141
Met Glu Glu Lys Glu Ser Val Cys Thr Leu Ser Lys Trp Ile Glu Val
305                 310                 315
CCG GAA GCA GTT CGT GTT TCG TAC AAA AAC AGT TAC CAC TTT TCA CTT       118
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Pro | Glu | Ala | Val | Arg | Val | Ser | Tyr | Lys | Asn | Ser | Tyr | His | Phe | Ser | Leu |      |
| 320 |     |     |     | 325 |     |     |     |     | 330 |     |     |     |     |     | 335 |      |
| AAA | GAT | ATG | ACT | ATG | ACG | TTC | TCG | TCC | GGA | AAA | CAA | CCT | TTT | AAC | ATC | 1237 |
| Lys | Asp | Met | Thr | Met | Thr | Phe | Ser | Ser | Gly | Lys | Gln | Pro | Phe | Asn | Ile |      |
| 340 |     |     |     | 345 |     |     |     |     | 350 |     |     |     |     |     |     |      |
| AGC | AGG | CTT | CAT | TTG | GCT | GAA | TGC | GTT | CCT | ACC | ATA | GCC | ACG | GAG | GCC | 1285 |
| Ser | Arg | Leu | His | Leu | Ala | Glu | Cys | Val | Pro | Thr | Ile | Ala | Thr | Glu | Ala |      |
| 355 |     |     |     | 360 |     |     |     |     | 365 |     |     |     |     |     |     |      |
| ATA | GAT | GGC | ATC | TTT | GCC | AGA | AAG | TAT | AGT | TCG | ACT | CAT | GTC | CGT | TCT | 1333 |
| Ile | Asp | Gly | Ile | Phe | Ala | Arg | Lys | Tyr | Ser | Ser | Thr | His | Val | Arg | Ser |      |
| 370 |     |     |     | 375 |     |     |     |     | 380 |     |     |     |     |     |     |      |
| GGG | GAC | ATC | GAA | TAC | TAT | CTC | GGT | AGT | GGC | GGA | TTT | CTG | ATC | GCA | TTT | 1381 |
| Gly | Asp | Ile | Glu | Tyr | Tyr | Leu | Gly | Ser | Gly | Gly | Phe | Leu | Ile | Ala | Phe |      |
| 385 |     |     |     | 390 |     |     |     |     | 395 |     |     |     |     |     |     |      |
| CAG | AAA | CTC | ATG | AGC | CAT | GGC | TTG | GCT | GAA | ATG | TAC | CTA | GAA | GAG | GCC | 1429 |
| Gln | Lys | Leu | Met | Ser | His | Gly | Leu | Ala | Glu | Met | Tyr | Leu | Glu | Glu | Ala |      |
| 400 |     |     |     | 405 |     |     |     |     | 410 |     |     |     |     |     | 415 |      |
| CAA | AGA | CAA | AAT | CAT | CTC | CCG | AGA | GGG | AGA | GAG | CGT | CGC | CAA | GCC | GCA | 1477 |
| Gln | Arg | Gln | Asn | His | Leu | Pro | Arg | Gly | Arg | Glu | Arg | Arg | Gln | Ala | Ala |      |
| 420 |     |     |     | 425 |     |     |     |     | 430 |     |     |     |     |     |     |      |
| GGT | CGC | CGC | ACG | GCG | TCG | CTG | CAG | TCT | GGA | CCT | CAG | GGT | GAT | AGA | ATT | 1525 |
| Gly | Arg | Arg | Thr | Ala | Ser | Leu | Gln | Ser | Gly | Pro | Gln | Gly | Asp | Arg | Ile |      |
| 435 |     |     |     | 440 |     |     |     |     | 445 |     |     |     |     |     |     |      |
| ACT | ACC | CAC | AGT | TCT | GCA | ACA | TTT | GCC | ATG | TTA | CAA | TTT | GCA | TAC | GAC | 1573 |
| Thr | Thr | His | Ser | Ser | Ala | Thr | Phe | Ala | Met | Leu | Gln | Phe | Ala | Tyr | Asp |      |
| 450 |     |     |     | 455 |     |     |     |     | 460 |     |     |     |     |     |     |      |
| AAA | ATC | CAA | GCC | CAT | GTT | AAC | GAG | CTT | ATC | GGA | AAT | TTG | TTG | GAA | GCG | 1621 |
| Lys | Ile | Gln | Ala | His | Val | Asn | Glu | Leu | Ile | Gly | Asn | Leu | Leu | Glu | Ala |      |
| 465 |     |     |     | 470 |     |     |     |     | 475 |     |     |     |     |     |     |      |
| TGG | TGT | GAG | CTT | CAG | AAC | CGC | CAA | CTG | ATT | GTA | TGG | CAT | GAG | ATG | AAG | 1669 |
| Trp | Cys | Glu | Leu | Gln | Asn | Arg | Gln | Leu | Ile | Val | Trp | His | Glu | Met | Lys |      |
| 480 |     |     |     | 485 |     |     |     |     | 490 |     |     |     |     |     | 495 |      |
| AAA | CTA | AAC | CCG | AAC | TCA | CTG | ATG | ACA | TCT | TTG | TTC | GGA | CAA | CCT | GTA | 1717 |
| Lys | Leu | Asn | Pro | Asn | Ser | Leu | Met | Thr | Ser | Leu | Phe | Gly | Gln | Pro | Val |      |
| 500 |     |     |     | 505 |     |     |     |     | 510 |     |     |     |     |     |     |      |
| AGC | GCC | AGG | CTA | TTG | GGA | GAC | ATC | GTA | GCG | GTA | TCA | AAA | TGT | ATA | GAA | 1765 |
| Ser | Ala | Arg | Leu | Leu | Gly | Asp | Ile | Val | Ala | Val | Ser | Lys | Cys | Ile | Glu |      |
| 515 |     |     |     | 520 |     |     |     |     | 525 |     |     |     |     |     |     |      |
| ATT | CCA | ATC | GAA | AAT | ATT | AGG | ATG | CAG | GAT | TCC | ATG | CGC | ATG | CCA | GGG | 1813 |
| Ile | Pro | Ile | Glu | Asn | Ile | Arg | Met | Gln | Asp | Ser | Met | Arg | Met | Pro | Gly |      |
| 530 |     |     |     | 535 |     |     |     |     | 540 |     |     |     |     |     |     |      |
| GAC | CCA | ACC | ATG | TGC | TAT | ACC | AGA | CCA | GTA | CTT | ATT | TTC | AGG | TAT | TCG | 1861 |
| Asp | Pro | Thr | Met | Cys | Tyr | Thr | Arg | Pro | Val | Leu | Ile | Phe | Arg | Tyr | Ser |      |
| 545 |     |     |     | 550 |     |     |     |     | 555 |     |     |     |     |     |     |      |
| TCC | TCC | CCT | GAG | TCA | CAG | TTT | TCT | GCG | AAC | TCA | ACA | GAA | AAC | CAC | AAT | 1909 |
| Ser | Ser | Pro | Glu | Ser | Gln | Phe | Ser | Ala | Asn | Ser | Thr | Glu | Asn | His | Asn |      |
| 560 |     |     |     | 565 |     |     |     |     | 570 |     |     |     |     |     | 575 |      |
| CTT | GAC | ATA | TTA | GGC | CAA | CTC | GGA | GAA | CAT | AAT | GAA | ATT | TTA | CAA | GGG | 1957 |
| Leu | Asp | Ile | Leu | Gly | Gln | Leu | Gly | Glu | His | Asn | Glu | Ile | Leu | Gln | Gly |      |
| 580 |     |     |     | 585 |     |     |     |     | 590 |     |     |     |     |     |     |      |
| GAA | CCA | TGC | ATG | ATC | AAT | CAC | AGA | CGG | TAC | TTT | CTG |     |     |     |     | 2005 |
| Arg | Asn | Leu | Ile | Glu | Pro | Cys | Met | Ile | Asn | His | Arg | Arg | Tyr | Phe | Leu |      |
| 595 |     |     |     | 600 |     |     |     |     | 605 |     |     |     |     |     |     |      |
| TTG | GGA | GAA | AAC | TAC | CTT | CTT | TAC | GAA | GAC | TAT | ACA | TTT | GTT | AGA | CAA | 2053 |
| Leu | Gly | Glu | Asn | Tyr | Leu | Leu | Tyr | Glu | Asp | Tyr | Thr | Phe | Val | Arg | Gln |      |
| 610 |     |     |     | 615 |     |     |     |     | 620 |     |     |     |     |     |     |      |
| GTA | AAT | GCT | TCC | GAG | ATC | GAA | GAA | GTG | AGC | ATA | TTC | ATC | AAC | TTG | AAC | 2101 |
| Val | Asn | Ala | Ser | Glu | Ile | Glu | Glu | Val | Ser | Ile | Phe | Ile | Asn | Leu | Asn |      |
| 625 |     |     |     | 630 |     |     |     |     | 635 |     |     |     |     |     |     |      |
| GCC | ACT | ATA | CTA | GAA | GAT | TTG | GAC | TTT | GTG | CCC | GTC | GAA | GTA | TAC | ACT | 2149 |
| Ala | Thr | Ile | Leu | Glu | Asp | Leu | Asp | Phe | Val | Pro | Val | Glu | Val | Tyr | Thr |      |
|     |     | 645 |     |     |     | 650 |     |     |     | 655 |     |     |     |     |     |      |
| CGC | GAG | GAA | CTC | AGA | GAT | ACT | GGG | ACT | TTA | AAC | TAT | GAT | GAT | GTG | GTC | 2197 |
| Arg | Asp | Thr | Gly | Thr | Leu | Asn | Tyr | Asp | Asp | Val | Val |     |     |     |     |      |
| 660 |     |     |     | 665 |     |     |     |     | 670 |     |     |     |     |     |     |      |
| AGA | TAT | CAA | AAT | ATT | TAT | AAC | AAA | AGG | TTC | AGA | GAC | ATT | GAC | ACT | GTA | 2245 |
| Arg | Tyr | Gln | Asn | Ile | Tyr | Asn | Lys | Arg | Phe | Arg | Asp | Ile | Asp | Thr | Val |      |
| 675 |     |     |     | 680 |     |     |     |     | 685 |     |     |     |     |     |     |      |
| ATA | CGT | GGA | GAT | AGG | GGA | GAT | GCA | ATC | TTT | AGA | GCA | ATA | GCA | GAT | TTT | 2293 |
| Ile | Arg | Gly | Asp | Arg | Gly | Asp | Ala | Ile | Phe | Arg | Ala | Ile | Ala | Asp | Phe |      |
| 690 |     |     |     | 695 |     |     |     |     | 700 |     |     |     |     |     |     |      |
| TTT | GGC | AAC | ACT | CTT | GGA | GAA | GTA | GGA | AAG | GCA | TTG | GGA | ACT | GTA | GTG | 2341 |
| Phe | Gly | Asn | Thr | Leu | Gly | Glu | Val | Gly | Lys | Ala | Leu | Gly | Thr | Val | Val |      |
| 705 |     |     |     | 710 |     |     |     |     | 715 |     |     |     |     |     |     |      |
| ATG | ACA | GCC | GCG | GCA | GCA | GTA | ATT | TCT | ACA | GTA | TCT | GGC | ATC | GCC | TCA | 2389 |
| Met | Thr | Ala | Ala | Ala | Ala | Val | Ile | Ser | Thr | Val | Ser | Gly | Ile | Ala | Ser |      |
| 720 |     |     |     | 725 |     |     |     |     | 730 |     |     |     |     |     | 735 |      |
| TTT | CTT | TCT | AAC | CCG | TTC | GCC | GCA | CTC | GGA | ATT | GGG | ATA | GCG | GTG | GTG | 2437 |
| Phe | Leu | Ser | Asn | Pro | Phe | Ala | Ala | Leu | Gly | Ile | Gly | Ile | Ala | Val | Val |      |
| 740 |     |     |     | 745 |     |     |     |     | 750 |     |     |     |     |     |     |      |
| GTG | AGC | ATT | ATT | TTA | GGA | CTG | CTG | GCG | TTC | AAA | TAT | GTA | ATG | AAC | CTG | 2485 |
| Val | Ser | Ile | Ile | Leu | Gly | Leu | Leu | Ala | Phe | Lys | Tyr | Val | Met | Asn | Leu |      |

| | | | | | | | | | | | | | | |
|---|---|---|---|---|---|---|---|---|---|---|---|---|---|---|
| 755 | | | | | 760 | | | | | 765 | | | | |
| AAA | TCA | AAC | CCA | GTT | CAG | GTT | CTG | TTC | CCA | GGC | GCA | GTT | CCC | CCG | GCC | 2533 |
| Lys | Ser | Asn | Pro | Val | Gln | Val | Leu | Phe | Pro | Gly | Ala | Val | Pro | Pro | Ala |
| 770 | | | | | 775 | | | | | 780 | | | | |
| GGA | ACT | CCT | CCA | CGA | CCC | TCT | AGA | CGT | TAC | TAC | AAG | GAT | GAG | GAG | GAG | 2581 |
| Gly | Thr | Pro | Pro | Arg | Pro | Ser | Arg | Arg | Tyr | Tyr | Lys | Asp | Glu | Glu | Glu |
| 785 | | | | | 790 | | | | | 795 | | | | |
| GTT | GAG | GAG | GAT | AGT | GAT | GAG | GAC | GAC | AGG | ATA | CTT | GCC | ACC | AGA | GTT | 2629 |
| Val | Glu | Glu | Asp | Ser | Asp | Glu | Asp | Asp | Arg | Ile | Leu | Ala | Thr | Arg | Val |
| 800 | | | | | 805 | | | | | 810 | | | | | 815 |
| CTG | AAA | GGC | CTT | GAG | CTT | CTA | CAC | AAG | GAT | GAA | CAG | AAA | GCT | CGA | AGA | 2677 |
| Leu | Lys | Gly | Leu | Glu | Leu | Leu | His | Lys | Asp | Glu | Gln | Lys | Ala | Arg | Arg |
| 820 | | | | | 825 | | | | | 830 | | | | |
| CAG | AAA | GCG | CGG | TTT | TCT | GCT | TTT | GCT | AAA | AAT | ATG | AGA | AAC | CTA | TTT | 2725 |
| Gln | Lys | Ala | Arg | Phe | Ser | Ala | Phe | Ala | Lys | Asn | Met | Arg | Asn | Leu | Phe |
| 835 | | | | | 840 | | | | | 845 | | | | |
| CGC | AGA | AAA | CCC | CGA | ACC | AAG | GAA | GAT | GAC | TAC | CCC | CTG | CTC | GAA | TAC | 2773 |
| Arg | Arg | Lys | Pro | Arg | Thr | Lys | Glu | Asp | Asp | Tyr | Pro | Leu | Leu | Glu | Tyr |
| 850 | | | | | 855 | | | | | 860 | | | | |
| CCT | TCG | TGG | GCA | GAA | GAA | AGC | GAA | GAC | GAA | TAAGTTTAAA | | TGCAGTTTAT | | | | 2823 |
| Pro | Ser | Trp | Ala | Glu | Glu | Ser | Glu | Asp | Glu | | | | | |
| 865 | | | | | 870 | | | | | |

| | | | | |
|---|---|---|---|---|
| TTAATAAAAT | GACATTACTA | TTCACATGAC | TCAGTCTGCC | ATCATTTGCG | CAAATGCGGC | 2883 |
| TGCTTCTTTC | TTTCTTTTCA | ATTTGTCTG | AGCATCTTTC | AGTCGTTTTG | GCATAGAAGC | 2943 |
| ATCGACTGTC | TCCCGAGCAG | ACTCTTGATT | ACTATTTTCT | AGTTCCTCTT | TTCTCTCTGA | 3003 |
| AGACGAATCG | GCATTGGAAG | CTGATTTAAG | ACCGGCAACC | TCTTTTTGAA | GGGTCAGAAT | 3063 |
| TC | | | | | | 3065 |

We claim:

1. An isolated nucleic acid molecule encoding the gB glycoprotein gene of Infectious Laryngotracheitis Virus having the sequence shown in SEQ ID NO: 1.

2. A recombinant vector comprising SEQ ID NO: 1.

3. The recombinant vector of claim 2, wherein the vector is an expression vector.

4. A recombinant avipox virus comprising SEQ ID NO: 1.

5. The recombinant avipox virus of claim 4 wherein the avipox is fowlpox virus.

6. A method of immunizing a fowl against infectious laryngotracheitis virus, comprising administering to the fowl an amount of the recombinant avipox virus of claim 4 effective to protect the fowl against symptoms of infectious laryngotracheitis virus disease.

7. The method of claim 6, wherein the recombinant avipox virus is fowlpox virus.

8. The method of claim 6, wherein the fowl is a chicken.

9. The method of claim 7, wherein the fowl is a chicken.

* * * * *

UNITED STATES PATENT AND TRADEMARK OFFICE
CERTIFICATE OF CORRECTION

PATENT NO. : 5,443,831  
DATED : August 22, 1995  
INVENTOR(S) : Calvin L. Keeler, et al Page 1 of 8

It is certified that error appears in the above-indentified patent and that said Letters Patent is hereby corrected as shown below:

At Columns 11 - 16 please delete SEQ ID NO: 1 and insert: --

```
GAATTCGACC TCGACGGCCC GATTTTGGAA AACGGGCTAT ATTTAACATT TGAAGAGGAA        60

CATCCATTAG TTGCAGTGTG GGGCGTCGAT GACCGCGGGA AACTGGGTCC AGCGTCTACT       120

ATCATAGTAG AGAAAGATTT ATACGCGGTC CTGTATGCAA TCCTACATCG CCGTGAACAT       180

TGAC ATG GCT AGC TTG AAA ATG CTG ATC TGC GTG TGC GTG GCA ATC CTG       229
     Met Ala Ser Leu Lys Met Leu Ile Cys Val Cys Val Ala Ile Leu
      1           5                  10                 15

ATC CCA TCT ACC CTA TCT CAA GAT TCA CAC GGA ATT GCT GGA ATA ATA       277
Ile Pro Ser Thr Leu Ser Gln Asp Ser His Gly Ile Ala Gly Ile Ile
                 20                  25                 30

GAC CCT CGT GAT ACA GCC AGC ATG GAT GTT GGA AAA ATC TCT TTC TCC       325
Asp Pro Arg Asp Thr Ala Ser Met Asp Val Gly Lys Ile Ser Phe Ser
             35                  40                  45

GAA GCC ATT GGG TCG GGG GCA CCG AAA GAA CCC CAG ATT AGA AAC AGA       373
Glu Ala Ile Gly Ser Gly Ala Pro Lys Glu Pro Gln Ile Arg Asn Arg
         50                  55                  60

ATT TTT GCG TGC TCA TCT CCA ACT GGC GCC AGT GTT GCG AGG CTT GCC       421
Ile Phe Ala Cys Ser Ser Pro Thr Gly Ala Ser Val Ala Arg Leu Ala
     65                  70                  75

CAG CCA CGA CAT TGT CAC CGA CAT GCC GAT TCG ACT AAC ATG ACT GAA       469
Gln Pro Arg His Cys His Arg His Ala Asp Ser Thr Asn Met Thr Glu
 80              85                  90                  95
```

UNITED STATES PATENT AND TRADEMARK OFFICE
CERTIFICATE OF CORRECTION

PATENT NO. : 5,443,831  Page 2 of 8
DATED : August 22, 1995
INVENTOR(S) : Calvin L. Keeler, et al It is certified that error appears in the above-indentified patent and that said Letters Patent is hereby corrected as shown below:

```
GGA ATT GCC GTA GTC TTC AAG CAA AAC ATT GCC CCG TAC GTC TTT AAT            517
Gly Ile Ala Val Val Phe Lys Gln Asn Ile Ala Pro Tyr Val Phe Asn
            100                 105                 110

GTG ACT CTA TAC TAT AAA CAT ATA ACC ACA GTT ACT ACG TGG GCA TTA            565
Val Thr Leu Tyr Tyr Lys His Ile Thr Thr Val Thr Thr Trp Ala Leu
            115                 120                 125

TTC TCA AGA CCC CAA ATA ACA AAT GAG TAC GTG ACC AGG GTT CCA ATA            613
Phe Ser Arg Pro Gln Ile Thr Asn Glu Tyr Val Thr Arg Val Pro Ile
            130                 135                 140

GAC TAT CAT GAA ATT GTC AGG ATT GAT CGA TCG GGA GAA TGC TCA TCC            661
Asp Tyr His Glu Ile Val Arg Ile Asp Arg Ser Gly Glu Cys Ser Ser
            145                 150                 155

AAA GCA ACG TAT CAT AAA AAT TTC ATG TTT TTT GAA GCT TAC GAC AAT            709
Lys Ala Thr Tyr His Lys Asn Phe Met Phe Phe Glu Ala Tyr Asp Asn
160             165                 170                 175

GAT GAA CGA GAA AAA AAA TTG CCC CTG GTT CCA TCA CTG TTA AGA TCA            757
Asp Glu Arg Glu Lys Lys Leu Pro Leu Val Pro Ser Leu Leu Arg Ser
            180                 185                 190

ACT GTC TCC AAG GCG TTT CAT ACA ACT AAC TTT ACT AAG CGA CAT CAA            805
Thr Val Ser Lys Ala Phe His Thr Thr Asn Phe Thr Lys Arg His Gln
            195                 200                 205

ACC CTG GGA TAC CGA ACG TCT ACA TCG GTC GAC TGT GTT GTG GAA TAT            853
Thr Leu Gly Tyr Arg Thr Ser Thr Ser Val Asp Cys Val Val Glu Tyr
            210                 215                 220
```

UNITED STATES PATENT AND TRADEMARK OFFICE
CERTIFICATE OF CORRECTION

PATENT NO. : 5,443,831  
DATED : August 22, 1995  
INVENTOR(S) : Calvin L. Keeler, et al Page 3 of 8

It is certified that error appears in the above-indentified patent and that said Letters Patent is hereby corrected as shown below:

```
CTA CAG GCT AGA TCT GTA TAC CCG TAT GAT TAC TTT GGA ATG GCG ACA        901
Leu Gln Ala Arg Ser Val Tyr Pro Tyr Asp Tyr Phe Gly Met Ala Thr
    225             230             235

GGT GAT ACA GTA GAA ATT TCT CCT TTT TAT ACC AAA AAC ACG ACC GGA        949
Gly Asp Thr Val Glu Ile Ser Pro Phe Tyr Thr Lys Asn Thr Thr Gly
240             245             250             255

CCA AGG CGT CAC AGT GTC TAC AGA GAC TAT AGA TTT CTC GAA ATC GCA        997
Pro Arg Arg His Ser Val Tyr Arg Asp Tyr Arg Phe Leu Glu Ile Ala
            260             265             270

AAT TAT CAA GTC AGG GAT TTG GAA ACC GGA CAA ATA AGA CCC CCT AAA       1045
Asn Tyr Gln Val Arg Asp Leu Glu Thr Gly Gln Ile Arg Pro Pro Lys
        275             280             285

AAA AGA AAC TTT CTA ACA GAT GAA CAA TTC ACT ATA GGC TGG GAT GCA       1093
Lys Arg Asn Phe Leu Thr Asp Glu Gln Phe Thr Ile Gly Trp Asp Ala
        290             295             300

ATG GAA GAA AAG GAA TCT GTA TGT ACT CTC AGT AAA TGG ATT GAA GTC       1141
Met Glu Glu Lys Glu Ser Val Cys Thr Leu Ser Lys Trp Ile Glu Val
    305             310             315

CCG GAA GCA GTT CGT GTT TCG TAC AAA AAC AGT TAC CAC TTT TCA CTT       1189
Pro Glu Ala Val Arg Val Ser Tyr Lys Asn Ser Tyr His Phe Ser Leu
320             325             330             335

AAA GAT ATG ACT ATG ACG TTC TCG TCC GGA AAA CAA CCT TTT AAC ATC       1237
Lys Asp Met Thr Met Thr Phe Ser Ser Gly Lys Gln Pro Phe Asn Ile
            340             345             350

AGC AGG CTT CAT TTG GCT GAA TGC GTT CCT ACC ATA GCC ACG GAG GCC       1285
Ser Arg Leu His Leu Ala Glu Cys Val Pro Thr Ile Ala Thr Glu Ala
            355             360             365
```

UNITED STATES PATENT AND TRADEMARK OFFICE
CERTIFICATE OF CORRECTION

PATENT NO. : 5,443,831

DATED : August 22, 1995

INVENTOR(S) : Calvin L. Keeler, et al

It is certified that error appears in the above-indentified patent and that said Letters Patent is hereby corrected as shown below:

```
ATA GAT GGC ATC TTT GCC AGA AAG TAT AGT TCG ACT CAT GTC CGT TCT          1333
Ile Asp Gly Ile Phe Ala Arg Lys Tyr Ser Ser Thr His Val Arg Ser
        370                 375                 380

GGG GAC ATC GAA TAC TAT CTC GGT AGT GGC GGA TTT CTG ATC GCA TTT          1381
Gly Asp Ile Glu Tyr Tyr Leu Gly Ser Gly Gly Phe Leu Ile Ala Phe
    385                 390                 395

CAG AAA CTC ATG AGC CAT GGC TTG GCT GAA ATG TAC CTA GAA GAG GCA          1429
Gln Lys Leu Met Ser His Gly Leu Ala Glu Met Tyr Leu Glu Glu Ala
400             405                 410                 415

CAA AGA CAA AAT CAT CTC CCG AGA GGG AGA GAG CGT CGC CAA GCC GCA          1477
Gln Arg Gln Asn His Leu Pro Arg Gly Arg Glu Arg Arg Gln Ala Ala
                420                 425                 430

GGT CGC CGC ACG GCG TCG CTG CAG TCT GGA CCT CAG GGT GAT AGA ATT          1525
Gly Arg Arg Thr Ala Ser Leu Gln Ser Gly Pro Gln Gly Asp Arg Ile
            435                 440                 445

ACT ACC CAC AGT TCT GCA ACA TTT GCC ATG TTA CAA TTT GCA TAC GAC          1573
Thr Thr His Ser Ser Ala Thr Phe Ala Met Leu Gln Phe Ala Tyr Asp
                450                 455                 460

AAA ATC CAA GCC CAT GTT AAC GAG CTT ATC GGA AAT TTG TTG GAA GCG          1621
Lys Ile Gln Ala His Val Asn Glu Leu Ile Gly Asn Leu Leu Glu Ala
465                 470                 475

TGG TGT GAG CTT CAG AAC CGC CAA CTG ATT GTA TGG CAT GAG ATG AAG          1669
Trp Cys Glu Leu Gln Asn Arg Gln Leu Ile Val Trp His Glu Met Lys
480                 485                 490                 495

AAA CTA AAC CCG AAC TCA CTG ATG ACA TCT TTG TTC GGA CAA CCT GTA          1717
Lys Leu Asn Pro Asn Ser Leu Met Thr Ser Leu Phe Gly Gln Pro Val
                500                 505                 510
```

UNITED STATES PATENT AND TRADEMARK OFFICE
CERTIFICATE OF CORRECTION

PATENT NO. : 5,443,831                            Page 5 of 8
DATED      : August 22, 1995
INVENTOR(S): Calvin L. Keeler, et al It is certified that error appears in the above-indentified patent and that said Letters Patent is hereby corrected as shown below:

```
AGC GCC AGG CTA TTG GGA GAC ATC GTA GCG GTA TCA AAA TGT ATA GAA       1765
Ser Ala Arg Leu Leu Gly Asp Ile Val Ala Val Ser Lys Cys Ile Glu
            515             520             525

ATT CCA ATC GAA AAT ATT AGG ATG CAG GAT TCC ATG CGC ATG CCA GGG       1813
Ile Pro Ile Glu Asn Ile Arg Met Gln Asp Ser Met Arg Met Pro Gly
        530             535             540

GAC CCA ACC ATG TGC TAT ACC AGA CCA GTA CTT ATT TTC AGG TAT TCG       1861
Asp Pro Thr Met Cys Tyr Thr Arg Pro Val Leu Ile Phe Arg Tyr Ser
    545             550             555

TCC TCC CCT GAG TCA CAG TTT TCT GCG AAC TCA ACA GAA AAC CAC AAT       1909
Ser Ser Pro Glu Ser Gln Phe Ser Ala Asn Ser Thr Glu Asn His Asn
560             565             570             575

CTT GAC ATA TTA GGC CAA CTC GGA GAA CAT AAT GAA ATT TTA CAA GGG       1957
Leu Asp Ile Leu Gly Gln Leu Gly Glu His Asn Glu Ile Leu Gln Gly
                580             585             590

CGG AAT TTG ATA GAA CCA TGC ATG ATC AAT CAC AGA CGG TAC TTT CTG       2005
Arg Asn Leu Ile Glu Pro Cys Met Ile Asn His Arg Arg Tyr Phe Leu
            595             600             605

TTG GGA GAA AAC TAC CTT CTT TAC GAA GAC TAT ACA TTT GTT AGA CAA       2053
Leu Gly Glu Asn Tyr Leu Leu Tyr Glu Asp Tyr Thr Phe Val Arg Gln
        610             615             620
```

UNITED STATES PATENT AND TRADEMARK OFFICE
CERTIFICATE OF CORRECTION

PATENT NO. : 5,443,831   Page 6 of 8
DATED : August 22, 1995
INVENTOR(S) : Calvin L. Keeler, et al It is certified that error appears in the above-indentified patent and that said Letters Patent is hereby corrected as shown below:

```
GTA AAT GCT TCC GAG ATC GAA GAA GTG AGC ATA TTC ATC AAC TTG AAC        2101
Val Asn Ala Ser Glu Ile Glu Glu Val Ser Ile Phe Ile Asn Leu Asn
625             630             635

GCC ACT ATA CTA GAA GAT TTG GAC TTT GTG CCC GTC GAA GTA TAC ACT        2149
Ala Thr Ile Leu Glu Asp Leu Asp Phe Val Pro Val Glu Val Tyr Thr
640             645             650             655

CGC GAG GAA CTC AGA GAT ACT GGG ACT TTA AAC TAT GAT GAT GTG GTC        2197
Arg Glu Glu Leu Arg Asp Thr Gly Thr Leu Asn Tyr Asp Asp Val Val
                660             665             670

AGA TAT CAA AAT ATT TAT AAC AAA AGG TTC AGA GAC ATT GAC ACT GTA        2245
Arg Tyr Gln Asn Ile Tyr Asn Lys Arg Phe Arg Asp Ile Asp Thr Val
            675             680             685

ATA CGT GGA GAT AGG GGA GAT GCA ATC TTT AGA GCA ATA GCA GAT TTT        2293
Ile Arg Gly Asp Arg Gly Asp Ala Ile Phe Arg Ala Ile Ala Asp Phe
        690             695             700

TTT GGC AAC ACT CTT GGA GAA GTA GGA AAG GCA TTG GGA ACT GTA GTG        2341
Phe Gly Asn Thr Leu Gly Glu Val Gly Lys Ala Leu Gly Thr Val Val
    705             710             715

ATG ACA GCC GCG GCA GCA GTA ATT TCT ACA GTA TCT GGC ATC GCC TCA        2389
Met Thr Ala Ala Ala Ala Val Ile Ser Thr Val Ser Gly Ile Ala Ser
720             725             730             735

TTT CTT TCT AAC CCG TTC GCC GCA CTC GGA ATT GGG ATA GCG GTG GTG        2437
Phe Leu Ser Asn Pro Phe Ala Ala Leu Gly Ile Gly Ile Ala Val Val
            740             745             750

GTG AGC ATT ATT TTA GGA CTG CTG GCG TTC AAA TAT GTA ATG AAC CTG        2485
Val Ser Ile Ile Leu Gly Leu Leu Ala Phe Lys Tyr Val Met Asn Leu
        755             760             765
```

UNITED STATES PATENT AND TRADEMARK OFFICE
CERTIFICATE OF CORRECTION

PATENT NO. : 5,443,831  
DATED : August 22, 1995  
INVENTOR(S) : Calvin L. Keeler, et al Page 7 of 8

It is certified that error appears in the above-indentified patent and that said Letters Patent is hereby corrected as shown below:

```
AAA TCA AAC CCA GTT CAG GTT CTG TTC CCA GGC GCA GTT CCC CCG GCC       2533
Lys Ser Asn Pro Val Gln Val Leu Phe Pro Gly Ala Val Pro Pro Ala
        770             775                 780

GGA ACT CCT CCA CGA CCC TCT AGA CGT TAC TAC AAG GAT GAG GAG GAG       2581
Gly Thr Pro Pro Arg Pro Ser Arg Arg Tyr Tyr Lys Asp Glu Glu Glu
    785             790                 795

GTT GAG GAG GAT AGT GAT GAG GAC GAC AGG ATA CTT GCC ACC AGA GTT       2629
Val Glu Glu Asp Ser Asp Glu Asp Asp Arg Ile Leu Ala Thr Arg Val
800             805                 810                 815

CTG AAA GGC CTT GAG CTT CTA CAC AAG GAT GAA CAG AAA GCT CGA AGA       2677
Leu Lys Gly Leu Glu Leu Leu His Lys Asp Glu Gln Lys Ala Arg Arg
            820                 825                 830

CAG AAA GCG CGG TTT TCT GCT TTT GCT AAA AAT ATG AGA AAC CTA TTT       2725
Gln Lys Ala Arg Phe Ser Ala Phe Ala Lys Asn Met Arg Asn Leu Phe
            835                 840                 845

CGC AGA AAA CCC CGA ACC AAG GAA GAT GAC TAC CCC CTG CTC GAA TAC       2773
Arg Arg Lys Pro Arg Thr Lys Glu Asp Asp Tyr Pro Leu Leu Glu Tyr
            850                 855                 860

CCT TCG TGG GCA GAA GAA AGC GAA GAC GAA TAAGTTTAAA TGCAGTTTAT         2823
Pro Ser Trp Ala Glu Glu Ser Glu Asp Glu
    865                 870
```

UNITED STATES PATENT AND TRADEMARK OFFICE
CERTIFICATE OF CORRECTION

PATENT NO. : 5,443,831
DATED : August 22, 1995
INVENTOR(S) : Calvin L. Keeler, et al It is certified that error appears in the above-indentified patent and that said Letters Patent is hereby corrected as shown below:

```
TTAATAAAAT GACATTACTA TTCACATGAC TCAGTCTGCC ATCATTTGCG CAAATGCGGC    2883
TGCTTCTTTC TTTCTTTTCA ATTTTGTCTG AGCATCTTTC AGTCGTTTTG GCATAGAAGC    2943
ATCGACTGTC TCCCGAGCAG ACTCTTGATT ACTATTTTCT AGTTCCTCTT TTCTCTCTGA    3003
AGACGAATCG GCATTGGAAG CTGATTTAAG ACCGGCAACC TCTTTTTGAA GGGTCAGAAT    3063
TC                                                                  3065
```

--.

Signed and Sealed this

Fourteenth Day of November, 1995

BRUCE LEHMAN

*Attest:*

*Attesting Officer*      Commissioner of Patents and Trademarks